US011266525B2

(12) United States Patent
Kaforey et al.

(10) Patent No.: US 11,266,525 B2
(45) Date of Patent: Mar. 8, 2022

(54) PATIENT WARMING DEVICE FOR SURGICAL PROCEDURES

(71) Applicant: Xodus Medical, New Kensington, PA (US)

(72) Inventors: Craig Kaforey, Allison Park, PA (US); Mark Kaforey, Murrysville, PA (US); Paul Lloyd, Pittsburgh, PA (US)

(73) Assignee: Xodus Medical, Inc., New Kensington, PA (US)

( * ) Notice: Subject to any disclaimer, the term of this patent is extended or adjusted under 35 U.S.C. 154(b) by 373 days.

(21) Appl. No.: 15/411,493

(22) Filed: Jan. 20, 2017

(65) Prior Publication Data

US 2017/0209305 A1  Jul. 27, 2017

Related U.S. Application Data

(60) Provisional application No. 62/281,390, filed on Jan. 21, 2016.

(51) Int. Cl.
*A61F 7/08* (2006.01)
*A61G 13/12* (2006.01)
(Continued)

(52) U.S. Cl.
CPC ............... *A61F 7/08* (2013.01); *A61F 7/007* (2013.01); *A61G 13/10* (2013.01); *A61G 13/126* (2013.01);
(Continued)

(58) Field of Classification Search
CPC .... A61F 7/08; A61F 7/007; A61F 2007/0086; A61F 2007/0093; A61F 2007/0096;
(Continued)

(56) References Cited

U.S. PATENT DOCUMENTS 2,764,150 A  9/1956  Ettinger et al.
2,835,902 A  5/1958  Fash
(Continued)

FOREIGN PATENT DOCUMENTS

JP  63224161 A  9/1988

OTHER PUBLICATIONS

Armstrong et al., "An Integrative Review of Pressure Relief in Surgical Patients", Aorn Journal, Mar. 2001, pp. 645-674, vol. 73, Issue 3.
(Continued)

*Primary Examiner* — Eun Hwa Kim
*Assistant Examiner* — Adam Z Minchella
(74) *Attorney, Agent, or Firm* — The Webb Law Firm (57) ABSTRACT

A single-use patient positioning and warming pad configured to be placed between a patient and an operating table during a surgical procedure is provided. The pad includes a viscoelastic foam body having a top portion and a bottom portion; a heating element at least partially disposed between the top portion and the bottom portion of the foam body; and an electrical connector having a proximal end portion enclosed within the foam body connected to the heating element and a distal end portion extending from the foam body, configured to directly or indirectly connect to a power source and/or control unit for the heating element. Optionally, the foam body is formed from a foam material having sufficient viscosity and resiliency to maintain positioning of the patient relative to the operating table during surgical procedures in which the operating table is moved to an inclined position.

16 Claims, 5 Drawing Sheets

(51) Int. Cl.
*A61F 7/00* (2006.01)
*A61G 13/10* (2006.01)
*A61F 7/02* (2006.01)

(52) U.S. Cl.
CPC .............. *A61F 2007/0071* (2013.01); *A61F 2007/0086* (2013.01); *A61F 2007/0093* (2013.01); *A61F 2007/0096* (2013.01); *A61F 2007/0288* (2013.01); *A61G 2210/90* (2013.01)

(58) Field of Classification Search
CPC ..... A61F 2007/0288; A61F 2007/0071; A61G 13/10; A61G 13/126; A61G 2210/90
See application file for complete search history.

(56) References Cited

U.S. PATENT DOCUMENTS

| | | | |
|---|---|---|---|
| 3,227,440 A | 1/1966 | Scott | |
| 3,512,190 A | 5/1970 | Buff | |
| 3,670,725 A | 6/1972 | Gaylord, Jr. | |
| 3,780,387 A | 12/1973 | Propst | |
| 4,135,504 A | 1/1979 | Spann | |
| 4,717,611 A | 1/1988 | Petrella et al. | |
| 4,840,362 A | 6/1989 | Bremer et al. | |
| 4,989,849 A | 2/1991 | Zupancic et al. | |
| 5,015,037 A | 5/1991 | Giblin et al. | |
| 5,054,142 A | 10/1991 | Owens | |
| 5,138,138 A | 8/1992 | Theilacker et al. | |
| 5,306,231 A | 4/1994 | Cullum et al. | |
| 5,324,911 A | 6/1994 | Cranston et al. | |
| 5,346,278 A | 9/1994 | Dehondt | |
| 5,362,302 A | 11/1994 | Jensen et al. | |
| 5,402,544 A | 4/1995 | Crawford et al. | |
| 5,448,790 A | 9/1995 | Saro et al. | |
| 5,628,078 A | 5/1997 | Pennington et al. | |
| 5,661,860 A | 9/1997 | Heitz | |
| 5,669,094 A | 9/1997 | Swanson | |
| 5,784,734 A | 7/1998 | Scott et al. | |
| 5,802,640 A | 9/1998 | Ferrand et al. | |
| 5,893,183 A | 4/1999 | Bechtold, Jr. | |
| 5,906,017 A | 5/1999 | Ferrand et al. | |
| 6,202,230 B1 | 3/2001 | Borders | |
| 6,237,172 B1 | 5/2001 | Morgan, Sr. | |
| 6,401,283 B2 | 6/2002 | Thomas et al. | |
| 6,484,334 B1 | 11/2002 | Borders et al. | |
| 6,516,483 B1 | 2/2003 | VanSteenburg | |
| 6,541,094 B1 | 4/2003 | Landvik et al. | |
| 6,568,010 B1 | 5/2003 | Ames | |
| 6,620,488 B2 | 9/2003 | Oguri et al. | |
| 6,622,727 B2 | 9/2003 | Perry | |
| 6,653,363 B1 | 11/2003 | Tursi, Jr. et al. | |
| 6,701,558 B2 | 3/2004 | VanSteenburg | |
| 6,754,923 B2 | 6/2004 | Borders et al. | |
| 6,772,764 B2 | 8/2004 | Chapman | |
| 6,817,363 B2 | 11/2004 | Biondo et al. | |
| 6,866,915 B2 | 3/2005 | Landvik | |
| 6,880,189 B2 | 4/2005 | Welling et al. | |
| 6,904,631 B2 | 6/2005 | Vrzalik et al. | |
| 6,924,467 B2 | 8/2005 | Ellis et al. | |
| 6,933,469 B2 | 8/2005 | Ellis et al. | |
| 6,957,461 B2 | 10/2005 | Osborne et al. | |
| 7,076,822 B2 | 7/2006 | Pearce | |
| 7,171,708 B2 | 2/2007 | Osborne et al. | |
| 7,189,214 B1 | 3/2007 | Saunders | |
| 7,240,384 B2 | 7/2007 | DuDonis | |
| 7,441,293 B1 | 10/2008 | Singer et al. | |
| 7,454,805 B2 | 11/2008 | Osborne et al. | |
| 7,552,493 B2 | 6/2009 | McNulty | |
| 7,555,794 B2 | 7/2009 | Zelnik et al. | |
| 7,603,730 B2 | 10/2009 | Zelnik | |
| 7,676,862 B2 | 3/2010 | Poulos et al. | |
| 7,731,282 B2 | 6/2010 | Leeds | |
| 7,731,283 B2 | 6/2010 | Leeds | |
| 7,757,318 B2 | 7/2010 | Poulos et al. | |
| 7,789,461 B2 | 9/2010 | Leeds | |
| 7,849,540 B2 | 12/2010 | Hill | |
| 7,971,298 B2 | 7/2011 | Kobuss et al. | |
| 8,011,045 B2 | 9/2011 | Skripps | |
| 8,151,387 B2 | 4/2012 | Osborne et al. | |
| 8,464,720 B1 | 6/2013 | Pigazzi et al. | |
| 8,510,885 B2 | 8/2013 | Dennis et al. | |
| 8,511,314 B2 | 8/2013 | Pigazzi et al. | |
| 8,539,621 B2 | 9/2013 | West | |
| 8,555,890 B2 | 10/2013 | Hiebert | |
| 9,161,876 B2 | 10/2015 | Pigazzi et al. | |
| 2002/0019654 A1* | 2/2002 | Ellis | A61F 7/007 607/98 |
| 2002/0096311 A1* | 7/2002 | Kushnir | A61F 7/02 165/46 |
| 2003/0218003 A1 | 11/2003 | Ellis et al. | |
| 2004/0044091 A1 | 3/2004 | Niederoest et al. | |
| 2004/0149711 A1* | 8/2004 | Wyatt | A61F 7/00 219/217 |
| 2004/0256381 A1* | 12/2004 | Haas | A61F 7/007 219/543 |
| 2005/0210595 A1 | 9/2005 | Di Stasio et al. | |
| 2006/0016016 A1 | 1/2006 | Hornbach | |
| 2006/0112490 A1 | 6/2006 | Chausse | |
| 2006/0118541 A1* | 6/2006 | Ellis | A61F 7/007 219/217 |
| 2006/0248650 A1 | 11/2006 | Skripps | |
| 2008/0010751 A1 | 1/2008 | Kemper et al. | |
| 2008/0178390 A1 | 7/2008 | DuDonis | |
| 2009/0025150 A1 | 1/2009 | Smalling et al. | |
| 2009/0275808 A1 | 11/2009 | DiMaio et al. | |
| 2010/0212087 A1 | 8/2010 | Leib et al. | |
| 2010/0275377 A1 | 11/2010 | West | |
| 2010/0281617 A1 | 11/2010 | Brun | |
| 2011/0092890 A1* | 4/2011 | Stryker | A61F 7/007 604/23 |
| 2011/0263950 A1 | 10/2011 | Larson et al. | |
| 2013/0174853 A1 | 7/2013 | Pigazzi et al. | |
| 2013/0174854 A1* | 7/2013 | Pigazzi | A61G 13/127 128/845 |
| 2013/0289150 A1 | 10/2013 | Hager et al. | |
| 2013/0327339 A1 | 12/2013 | Chua | |
| 2015/0238021 A1 | 8/2015 | Wassermann | |
| 2015/0289817 A1 | 10/2015 | Augustine et al. | |
| 2016/0067135 A1 | 3/2016 | Pigazzi et al. | |
| 2017/0258630 A1* | 9/2017 | Pedro | A61G 13/121 |

OTHER PUBLICATIONS

Klauschie et al., "Use of Anti-Skid Material and Patient-Positioning to Prevent Patient Shifting during Robotic-Assisted Gynecologic Procedures", The Journal of Minimally Invasive Gynecology, Jul./Aug. 2010, pp. 504-507, vol. 17, No. 4.
Meridian Medical, Brochure and Specification Sheet, Surgical Positioners, "Trendelenburg Static Torso Pad", Apr. 3, 2012, 7 pages.
Walton-Geer, "Prevention of Pressure Ulcers in the Surgical Patient", Aorn Journal, Mar. 2009, pp. 538-552, vol. 89, No. 3.
Office Action issued in EP17742017.1 dated Sep. 23, 2020.

* cited by examiner

PATIENT WARMING DEVICE FOR SURGICAL PROCEDURES

CROSS-REFERENCE TO RELATED APPLICATION

This application claims priority to U.S. Provisional Patent Application No. 62/281,390 filed Jan. 21, 2016, entitled "Patient Warming Device for Surgical Procedures", the disclosure of which is hereby incorporated in its entirety by reference.

BACKGROUND

Field of the Invention

The invention relates generally to pads, cushions, pillows, and supports for cushioning and positioning a patient's body during a surgical procedure and, specifically, to a viscoelastic foam pad configured to support a patient during procedures in which a surgical table is inclined, including a heating element for warming the patient during the procedure.

Description of Related Art

Maintaining patient normothermia (e.g., normal body temperature) can be critical for preventing patient complications in the hospital operating room environment. Maintaining patient body temperature has been a challenge for healthcare workers, and is an important issue in assuring patient safety.

There are various devices and methods available to be used for warming a patient. One know method is simply to cover the patient with a blanket. However, a blanket may not be effective to warm a patient, as it depends solely on the patient's body heat, which may not be sufficient to maintain normothermia. Thus, in some cases, it can be desirable to provide heat from a source that is external to a patient. An example of a device including an artificial or external heating element is the Bair Hugger® manufactured by 3M Corporation, which blows heated air into an augmented warming blanket by means of an external blower.

However, both conventional and augmented warming blankets have substantial drawbacks. For example, any warming device that covers a patient may restrict access to a surgical site by a surgeon or operating room staff. Additionally, the Bair Hugger® requires the use of a blower, which physically heats and forces air into and through compartments of the augmented blanket. Use of a blower may increase noise in an operating room. Further, the blower may distribute dust, debris, and airborne contaminants throughout the operating room, which can create infection and/or contamination risks during the surgical procedure. Blowers also may be awkward to position during a surgical procedure and may obstruct surgeons or operating room staff while they attempt to perform their duties during surgery. While a blower might include an air filter, filters need to be cleaned or changed periodically. In addition, no filter is 100 percent effective, and even filtered air blowers create exhaust which may further contribute to migration of contaminants in an operating room.

Other methods and devices for warming a patient include multi-use cushioning and positioning devices, such as surgical beds, operating tables, and mattresses, which include a non-permeable cover or outer layer so that the device can be cleaned between uses. While such a layer may contribute to the longevity of the device over multiple uses, it has the detriment of allowing fluid to pool against the skin of the patient. Such layers also do not allow air to reach the skin of a patient. These detriments may contribute to the breakdown of the patient's skin, especially over the course of a lengthy surgical procedure. This risk is further exacerbated if the patient is elderly, diabetic, or otherwise susceptible to skin breakdown.

Reusable heating devices are also known in the art. Such reusable devices are exposed to multiple patients and require cleaning between uses. Cleaning requires time to be expended by operating room staff and may not be effective to reduce or eliminate the risk of the spread of infection.

For these reasons, a need exists for an efficient and effective way provide heat to a patient undergoing a surgical procedure, which does not cover the patient and does not require an air blower device. There is also a need for a cushion or pad that is breathable, does not allow fluid to pool against a patient's skin, and is less harsh to the skin of a patient undergoing a surgical procedure. A single-use device would increase hygiene, reduce risk of infection, and reduce set up and cleaning time by operating room staff.

SUMMARY

Generally provided herein is a patient warming pad, device, and system which are configured to maintain patient normothermia efficiently and effectively, without restricting access to a surgical site, by providing conductive and/or radiative heating from beneath the patient. In a non-limiting embodiment, the patient warming device is configured to include a single-use warming pad that is positioned beneath a patient during a surgical procedure.

According to an aspect of the disclosure, a single-use patient positioning and warming pad configured to be placed between a patient and an operating table during a surgical procedure is provided. The pad comprises a viscoelastic foam body comprising a top portion and a bottom portion; a heating element at least partially disposed between the top portion and the bottom portion of the foam body; and an electrical connector having a proximal end portion enclosed within the foam body connected to the heating element and a distal end portion extending from the foam body, configured to directly or indirectly connect to a power source and/or control unit for the heating element.

In some examples, the foam body comprises a foam material having sufficient viscosity and resiliency to maintain positioning of the patient relative to the operating table during surgical procedures in which the operating table is moved to an inclined position.

In some examples, during the surgical procedure the patient is placed in one or more of the following: an inclined position, a reverse inclined position, a Trendelenburg position, the reverse Trendelenburg position, and a modified Trendelenburg position. For example, an angle of the operating table in the inclined position can be between about 30 degrees and 45 degrees. In one particular example, the viscoelastic foam comprises a viscoelastic polyurethane having one or more of: a ball rebound in the range of approximately 0.1 percent to approximately 1.9 percent; a compression set, for a 25 percent compression, of less than 0.5 percent; an air flow in the range of 0.3 to 1.0 cubic foot per minute; an indentation force deflection in the range of approximately 10 to approximately 15 pounds; a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter.

Optionally, the pad further comprises a hermetically sealed protective sleeve enclosing at least a portion of the heating element to protect the heating element from a substances contained the pad. The pad may also include a heat reflective cover disposed on the bottom surface of the viscoelastic foam body.

In some examples, the pad further comprises one or more temperature sensors positioned within the foam body for measuring a temperature of the foam body which is warmed by the heating element. In that case, the pad may also include one or more cables at least partially enclosed within the foam body and extending between the one or more temperature sensors and the electrical connector.

In some examples, the top portion and/or the bottom portion of the foam body comprises at least an open cell foam portion. The top portion and/or the bottom portion of the foam body may also include a closed cell foam portion.

According to another aspect of the disclosure, a patient warming system is provided. The patient warming system includes a single-use patient positioning and warming pad configured to be placed between a patient and an operating table during a surgical procedure. The pad includes: a viscoelastic foam body comprising a top portion and a bottom portion; a heating element at least partially disposed between the top portion and the bottom portion of the foam body; and an electrical connector having a proximal end portion enclosed within the foam body connected to the heating element and a distal end portion extending from the foam body and configured to directly or indirectly connect to a power source and/or control unit for the heating element. The system also includes a control unit operatively connected to the warming pad and configured to control power provided to the heating element from a power source. The control unit includes: a cable removably connected to the electrical connector of the heating element for providing power and/or operating instructions to the heating element and a processor having computer-readable memory containing instructions. When executed by the processor, the instructions cause the processor to: receive and process information representative of a temperature information from the at least one temperature senor; determine a temperature of the warming and positioning pad based on the received and processed information; compare the determined temperature to, a threshold temperature value; and provide a notification to a user when the determined temperature exceeds the threshold value.

In some examples, the foam body comprises a foam material having sufficient viscosity and resiliency to maintain positioning of the patient relative to the operating table during surgical procedures in which the operating table is moved to an inclined position.

In some examples, the instructions further cause the processor to one of: increase a power output of the control unit to the heating element when the determined temperature is less than the threshold value; and decrease a power output of the control unit to the heating element when the determined temperature exceeds the threshold value.

In some examples, the surgical procedure performed for the patient comprises one or more of an inclined position, a reverse inclined position, a Trendelenburg position, the reverse Trendelenburg position, and a modified Trendelenburg position. For example, an angle of the operating table in the inclined position may be between about 30 degrees and 45 degrees.

In some examples, the viscoelastic foam comprises a viscoelastic polyurethane having one or more of: a ball rebound in the range of approximately 0.1 percent to approximately 1.9 percent; a compression set, for a 25 percent compression, of less than 0.5 percent; an air flow in the range of 0.3 to 1.0 cubic foot per minute; an indentation force deflection in the range of approximately 10 to approximately 15 pounds; a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter.

In some examples, the control unit includes a display, and wherein the instructions cause the processor to cause the display to display the determined temperature of the warming pad. Additionally, in some examples, providing the notification to the user when the determined temperature exceeds the threshold value can include causing the display to display a visual indication that the temperature of the positioning and warming pad is excessive.

According to another aspect of the disclosure, a method of warming a patient during a surgical procedure is provided. The method includes: placing single-use patient positioning and warming pad on an operating table; positioning the patient on the warming pad; actuating a heating element of the warming pad, thereby causing the warming pad to generate heat directed to the patient; and disposing of the warming pad after a use. The warming pad includes: a viscoelastic foam body comprising a top portion and a bottom portion; the heating element at least partially disposed between the top portion and the bottom portion of the foam body; and an electrical connector having a proximal end portion enclosed within the foam body connected to the heating element and a distal end portion extending from the foam body and configured to directly or indirectly connect to a power source and/or control unit for the heating element.

In some examples, the method also includes adjusting an incline of the operating table to an angle of 45 degrees or less, to place the patient in an inclined surgical position.

In some examples, the viscoelastic foam comprises a viscoelastic polyurethane having one or more of: a ball rebound in the range of approximately 0.1 percent to approximately 1.9 percent; a compression set, for a 25 percent compression, of less than 0.5 percent; an air flow in the range of 0.3 to 1.0 cubic foot per minute; an indentation force deflection in the range of approximately 10 to approximately 15 pounds; a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter.

In some examples, the method further includes adjusting a level of power provided from the control unit to the heating element to provide sufficient warmth from the pad to the patient to maintain the patient's normal body temperature.

In other examples, a patient warming device includes a patient warming pad configured to be positioned beneath a patient during a surgical procedure, wherein the patient warming pad has a heating element disposed in at least one foam portion, and wherein the hearing element is operatively connected to a heating element that is configured to control power provided to the heating element from a power source.

Optionally, the at least one foam portion comprises a top portion and a bottom portion, wherein the top portion and the bottom portion are comprised of viscoelastic foam, and wherein the heating element is disposed between the top portion and the bottom portion.

In other examples, the patient warming device may include a configuration wherein the heating element is separated from the top portion and the bottom portion by a sleeve. An embodiment may include a reflective layer that is positioned between the heating element and the bottom portion.

In other examples, the patient warming device may include a configuration, wherein the patient warming pad comprises at least one temperature sensor, wherein the at least one temperature sensor is operatively connected to the control unit.

In other examples, the patient warming pad includes at least one single-use foam layer that covers or encompasses a heating element. The at least one foam layer may include an upper layer and a lower layer, both comprised of a soft viscoelastic foam. The heating element may be disposed between the upper layer and a lower layer of foam. In an embodiment, the heating element further may be disposed in a thermally viable cover able to conduct heat through the foam and to the patient. The heating element may be controlled via an external control unit. In an embodiment, the control unit includes multiple settings to permit optimal thermal settings for various patient applications. The control unit also may contain safety factors for controlling the unit in the event of a fault.

In other aspects, as described herein, this application also relates to methods for warming a patient during a surgical procedure. The method can include placing a patient warming pad on an operating table, positioning a patient on the patient warming pad, setting a desired temperature for the heating element on the control unit, and heating the warming pad to the desired temperature to maintain a condition of normothermia in the patient.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Patient Warming Pad

Figure 1:
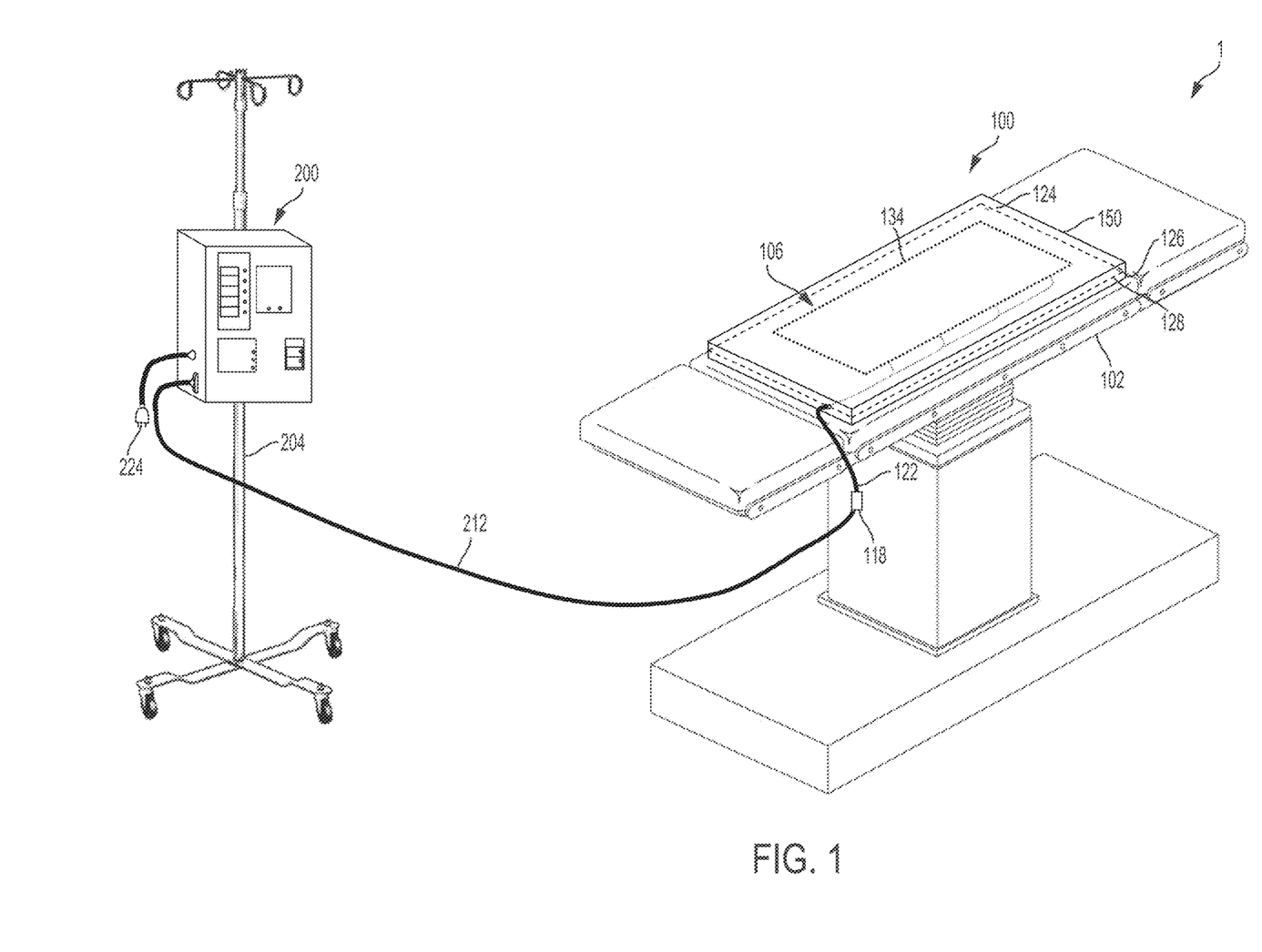
FIG. 1 is a perspective view of an embodiment of a patient warming device.

FIG. 1 shows an embodiment of a patient warming system 1 including warming pad 100 and control unit 200. In one example, the pad 100 is about 20 to 40 inches long or greater, about 20 to 28 inches wide, and about 1 to 3 inches thick, preferably about 1.5 inches thick. In some examples, the pad 100 can be a full-length pad which extends the full length of the operating table and/or is long enough to support the patient's entire body (e.g., about 60 inches to 72 inches). The warming pad 100 is positioned on an operating table 102 and configured to be placed beneath a patient undergoing a surgical procedure. In an embodiment, a patient lies directly on the warming pad 100. In other examples, an additional cover, layer, or cushioning materials may be positioned between the patient and the warming pad 100. For example, a lift sheet may be placed on top of the pad 100.

During a surgical procedure, the warming pad 100 is placed on the operating table 102. The patient and, in some cases, the cover or lift sheet are lowered onto the operating table 102, so that the pad 100 is situated between the patient and operating table 102. The pad 100 may or may not contact the skin of a patient. As described herein, the pad 100 is configured to at least partially conform to the patient's body shape and, in particular, to form depressions under the patient's body weight for maintaining the patient's body position on the pad 100. In addition, the pad 100 is configured to provide comfort and to prevent injuries, such as pressure sores, tissue damage, skin breakdown, and muscle damage, which may occur when the patient's skin contacts hard, rigid surfaces for extended periods of time. As described herein, once in position beneath the patient, the pad 100 is warmed by actuating a heating element 106 enclosed within the pad 100. During a surgical procedure, a level of power provided to the heating element 106 can be modified to adjust heat or warmth emitted from the pad 100, thereby controlling the patient's body temperature during surgery.

Foam Body

The warming pad 100 comprises a foam body 150 formed from one or more layers of flexible foam materials, such as polyurethane foam, viscoelastic foam, and/or gel foam. Material properties of the foam body 150 can be selected to aid in positioning a patient. For example, properties including foam viscosity, density, rebound, and others may be considered in selecting the foam for the warming pad 100. In some examples, a viscoelastic pad formed from viscoelastic polyurethane will have one or more of the following mechanical properties: a ball rebound in the range of approximately 0.1 percent to approximately 1.9 percent; a compression set (22 hrs@ 70° C.), for a 25 percent compression, of less than 0.5 percent (ASTM D-3574); an air flow in the range of 0.3 to 1.0 cubic foot per minute (ASTM D-3574); an indentation force deflection in the range of approximately 10 to approximately 15 pounds, and preferably about 11 pounds (ASTM D-3574); a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter, and preferably about 93 kilograms per cubic meter (ASTM D-3574).

In some examples, foam of the foam body 150 has the benefit of being sufficiently flexible to be used in surgical procedures requiring adjustable operating tables, or in extreme positions, such as at an incline or a reverse incline, or in Trendelenburg, reverse Trendelenburg, or modified Trendelenburg positions. For example, when placing the patient in the inclined position, the operating table may be elevated to an angle of between 0 degrees and 45 degrees relative to the horizontal, preferably to an elevation of between 15 degrees and 45 degrees relative to the horizontal, and more preferably to an elevation of between 30 degrees and 45 degrees relative to the horizontal. The foam of the warming pad 100 is generally selected to obtain favorable patient positioning results, in particular, to form a depression when the patient's weight is exerted on the top surface of the pad 100. The depth and surface area of the depression assists in maintaining patient position. For example, the sidewall and lip of the depression amount to structural supports that prevent or restrict a patient lying on the pad 100 from sliding on the operating table 102 during a surgical procedure. In addition, in some examples, the foam body may comprise a high viscosity foam which further limits patient movement or sliding. Such foams, as are known in the art, are generally referred to as memory or viscoelastic foams. In further examples, the surface of the foam may have a high coefficient of static friction, stickiness, or tackiness. As a result of such surface properties, the patient may, in effect, stick to the pad 100, thereby further limiting patient movement.

In some examples, the foam utilized for the construction of the warming pad 100 may comprise an open cell structure. Since fluids, such as gases and liquids, can pass through the open cell foam, the pad 100 is breathable, allowing at least some flow of air on the skin of a patient. Further, the porous open cell structure is at least partially permeable to fluids, which prevents fluids from pooling against the skin of a patient. As discussed herein, pooling of fluids and prolonged contact between pooled fluids and patient skin can cause tissue damage, pressure sores, skin deterioration, and similar conditions. The porous open cell structure may also contribute to insulation and heat transferring properties of the warming pad 100. For example, the porous open cell foam can be an insulator which separates the patient's body from cool structures, such as the surface of a metal operating table. The foam open cell structure also permits heat transfer from the heating element through the pad to the patient. As such, the foam structure contributes to maintaining the patient's body temperature.

Foam pads, such as the warming pad 100, can be manufactured relatively inexpensively compared with more robust patient positioning and/or warming systems (e.g., systems which are integrated with surgical beds or mattresses). Therefore, foam pads, such as the warming pad 100 disclosed herein, can be made as single-use, disposable products, which are used a single time on a single patient and then discarded. Advantageously, single-use products increase the hygiene of an operating room and reduce risk of infection, operating room preparation time, and clean-up time.

Additional details about exemplary viscoelastic foam pads having suitable material parameters for patient positioning, and which can be adapted for use as a patient warming pad in accordance with the present invention, are disclosed in U.S. Pat. No. 8,464,720 to Pigazzi et al., entitled "METHOD OF SECURING A PATIENT ONTO AN OPERATING TABLE WHEN THE PATIENT IS IN THE TRENDELENBURG POSITION AND APPARATUS THEREFOR INCLUDING A KIT" and U.S. Pat. No. 8,511,314 to Pigazzi et al., entitled "METHOD OF SECURING A PATIENT ONTO AN OPERATING TABLE WHEN THE PATIENT IS IN THE TRENDELENBURG POSITION AND APPARATUS THEREFOR INCLUDING A KIT", each of which is incorporated by reference herein.

Figure 2A:
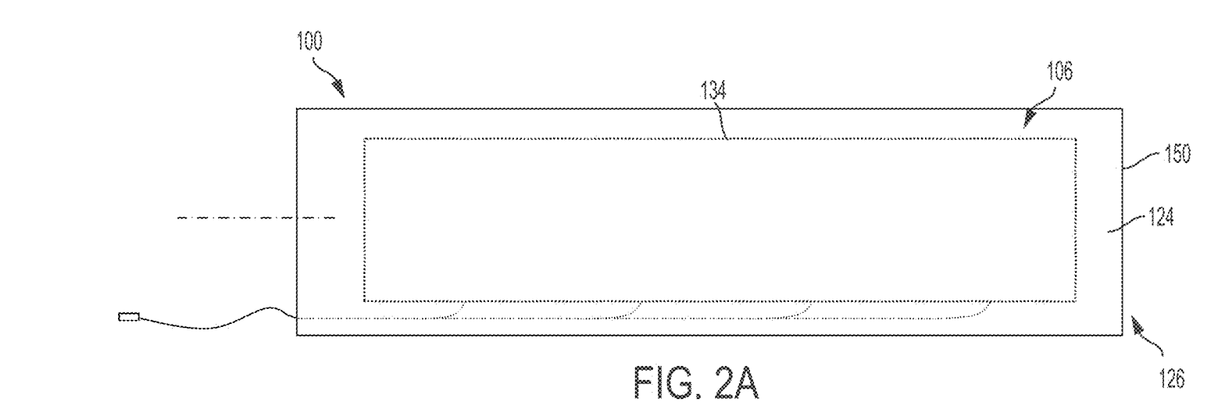
FIG. 2A is a top view of an embodiment of a warming pad of a patient warming device.
Figure 2B:
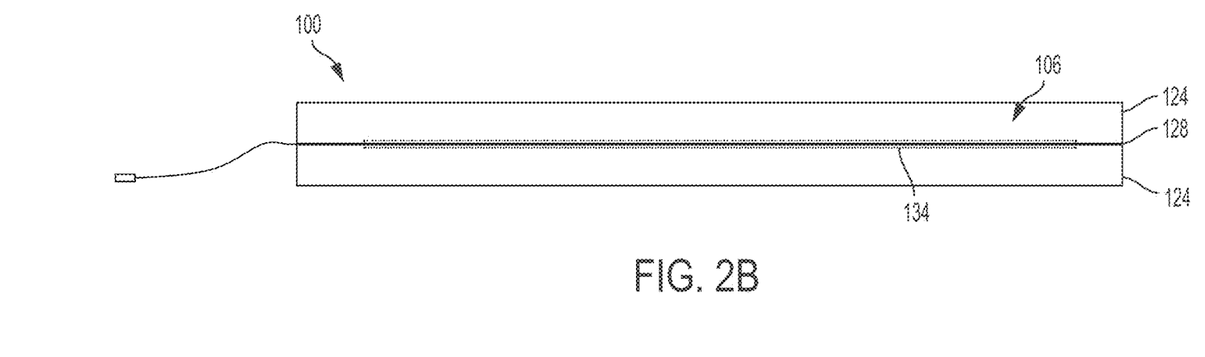
FIG. 2B is a side view of an embodiment of a warming pad of a patient warming device.

With reference to FIGS. 2A and 2B, in some examples, the foam body 150 of the warming pad 100 includes a top foam block or top portion 124 and a bottom foam block or bottom portion 126 mounted together by, for example, a synthetic adhesive 128 (shown in FIG. 2B). The top portion 124 and the bottom portion 126 may each comprise a single foam layer or multiple foam layers mounted together. The top portion 124 and the bottom portion 126 of the foam body 150 may each comprise the same material having substantially identical material properties. In other examples, the top portion 124 and bottom portion 126 can be formed from different foam materials having different material properties. In that case the materials of the respective foam portions 124, 126 are selected to provide different properties or qualities for the pad 100. For example, the top portion 124 may be a softer, more flexible, or less dense foam for cushioning and to ensure that a suitable depression for patient positioning can be created. The bottom portion 126 may be formed from a firmer or denser foam to provide structural support for the pad 100 and/or electronic heating components contained therein. In a similar manner, the top portion 124 and the bottom portion 126 may have substantially similar thicknesses or differing thicknesses depending on the type of surgical procedure or the size of the patient. For example, a thicker foam portion 124, 126 may be needed to provide increased cushioning for longer duration surgical procedures and/or for larger patients. As discussed hereinabove, a total thickness of the foam body 150 is about 1 to 3 inches thick.

Heating Element

As shown in FIGS. 1-4, the heating element 106 is disposed between the top portion 124 and the bottom portion 126 of the foam body 150. For example, the top portion 124 and the bottom portion 126 may be joined to encompass the heating element 106, and to allow access of power and/or signal leads 122 to heating element 106. The heating element 106 can be configured to provide heat to substantially the entire surface of the top portion 124 of the foam body 150. In other examples, the heating element 106 may be configured to provide heat only to a specific portion of the surface area of top portion 124. In an embodiment, heating element 106 may be separated from direct contact with a patient's skin by at least one layer of foam.

The heating element 106 includes one or more conductive elements 134. Conductive elements 134 may be comprised of stranded or twisted copper wire, or some other conductive materials known in the art. Conductive elements 134 may operatively connect to power and/or signal leads 122. Conductive elements 134 may heat heating element 106 by resistance, impedance, or any other manner known in the art. Conductive elements 134 may be arranged in heating element 106 in a variety of patterns, including loops, lines, and serpentine patterns. Individual conductive elements 134 may be arranged in similar or differing patterns. General dimensions and positioning of an exemplary rectangular or loop shaped heating element 106 are shown by dashed lines in FIGS. 1 and 2A.

It should be understood that heating element 106 is not limited to the above embodiment or embodiments. In another, non-limiting embodiment the heating element 106 may use an exothermic chemical reaction to produce heat. In other embodiments of heating element 106, the heating element 106 may comprise tubes for conducting heated fluid through the pad 100. For example, heated fluid may pass through warming pad 100 in rubber or plastic tubes, or another manner known in the art. Other non-limiting embodiments of the heating element 106 may include one or more carbon polymer sheets and/or carbon fibers embedded in a foam substrate.

The heating element 106 may be operatively connected to the control unit 200 by cables or cords, such as the power or signal lead 122 extending from the heating element 106 enclosed in the pad 100 to a socket, outlet, or connector 118 outside of the pad 100. As shown in FIG. 1, the connector 118 can be connected to a power and/or signal lead 212 extending from a suitable socket or outlet of the control unit 200 to establish an electrical connection between the control unit 200 and heating element 106. As a result of the electrical connection, the control unit 200 provides power and, in some cases, operating instructions to the heating element 106 through leads 122, 212. Desirably, the leads 122, 212 can be disconnected from the control unit 200 and from each other. For example, a user may disconnect the connector 118 from the power and signal lead 212 after a surgical procedure is completed and the patient has been lifted from the pad 100. The leads 212 may be reused by connecting them to an appropriate connector 118 of another pad 100. The leads 122 and electrical components connected thereto can be single use components that are used by one patient and then discarded along with the pad 100. Beneficially, the leads 122 and other portions of the warming pad 100 do not need to be cleaned or disinfected following use by a patient. Instead, these items may be simply discarded and a new warming pad 100 and attached leads 122 may be obtained for the next patient.

Figure 3:
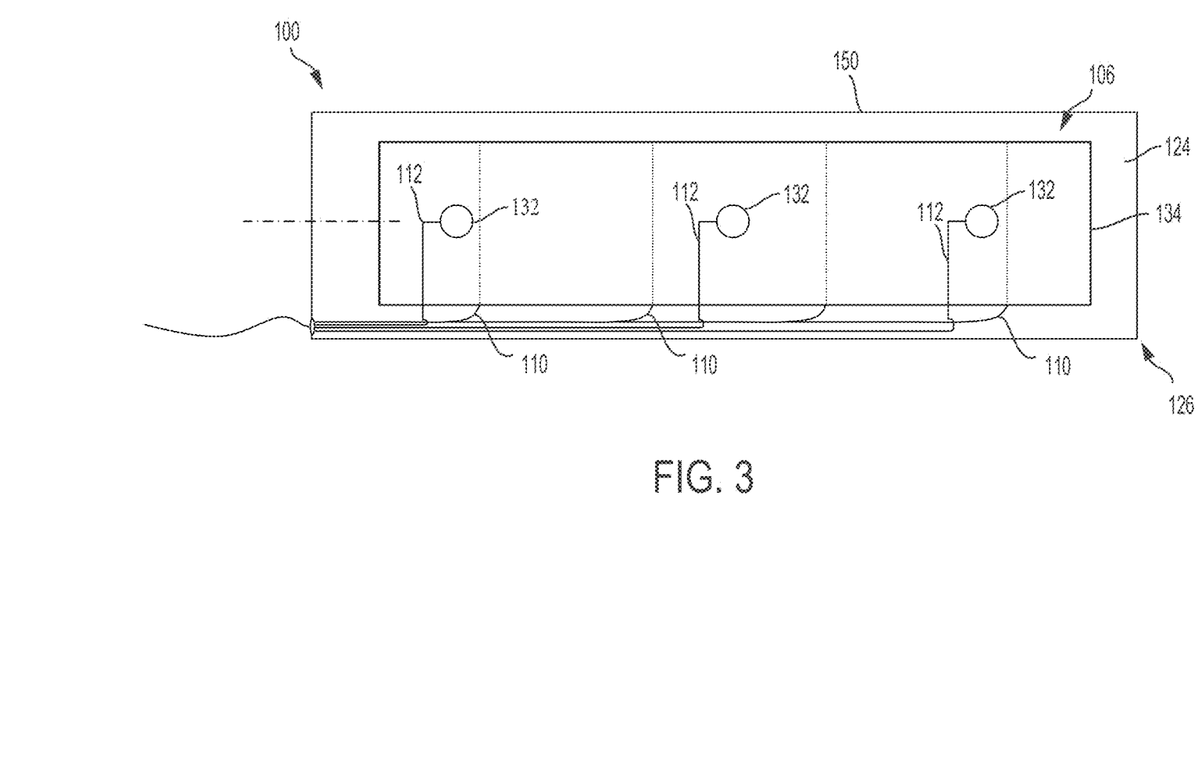
FIG. 3 is a cross-sectional top view of an embodiment of a warming pad of a patient warming device.

FIG. 3 illustrates another arrangement of the heating element 106, disposed within the foam body 150. As shown in FIG. 3, the heating element 106 may include at least one temperature sensor 132, such as a commercially available thermocouple. The at least one temperature sensor 132 may be operatively connected to the control unit 200 via power and/or signal leads 122, 212 and provide temperature data of the heating element 106 or warming pad 100 to a processor associated with the control unit 200 (shown in FIG. 1). The processor can be a conventional general-purpose microprocessor for a computer, tablet, or smartphone device, as are known in the art. The processor includes or is associated with transitory and non-transitory computer readable memory with instructions that, when executed by the processor, control operation of the control unit 200, heating element 106, and other aspects of the warming pad 100. Temperature data obtained by the temperature sensor 132 may be displayed on control unit 200, and be used by operating room staff to maintain the temperature of warming pad 100 within a safe temperature range. In some examples, a suitable temperature range for the pad 100 is between about 37° C. and 42° C. As described herein, temperature data from the at least one temperature sensor 132 also may be used by a processor in the control unit 200 to automatically monitor the warming pad 100 and maintain the temperature thereof within the safe range. The processor may also cause the control unit 200 to provide a notification and/or warning to a user if a measured temperature is greater than a maximum allowable temperature or target value.

Figure 4:
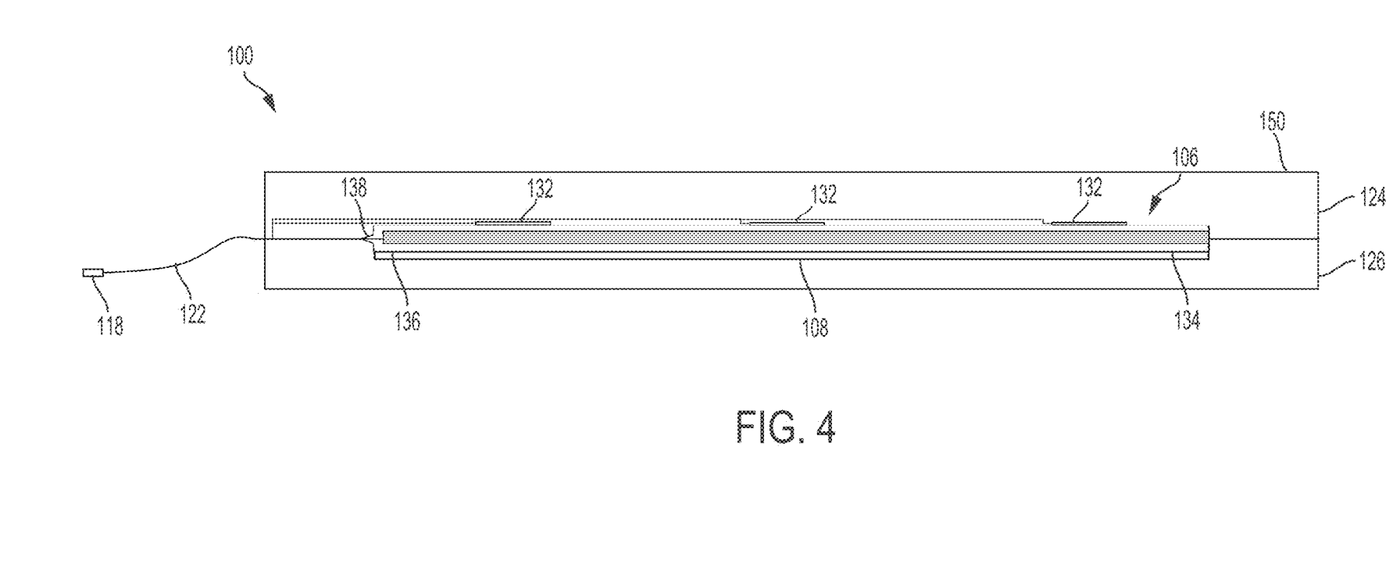
FIG. 4 is cross-sectional side view of an embodiment of a warming pad of a patient warming device.

FIG. 4 shows a cross-sectional side view of another embodiment of the warming pad 100. As shown in FIG. 4, the top portion 124 of the foam body 150 is positioned above and in contact with the bottom portion 126. As discussed herein, the portions 124, 126 may be held together by a suitable synthetic adhesive, such as adhesive 128. The top portion 124 and the bottom portion 126 contain or enclose the heating element 106 and multiple temperature sensors 132. The heating element 106 and temperature sensors 132 may be electrically connected to power and/or signal leads 122. In some examples, as shown in FIG. 4, the power and/or sensor leads 122 split inside warming pad 100, such that a power lead 110 connects to heating element 106 and a signal lead 112 connects to at least one temperature sensor 132. However, it should be understood that other configurations of leads 122, 110, and 112 may be used to operatively connect heating element 106 and/or at least one temperature sensor 132 to a power source and/or the control unit 200.

With continued reference to FIG. 4, heating element 106 may be situated within a sleeve 136. The sleeve 136 may provide insulation of heating element 106. In an embodiment, the sleeve 136 may be a hermetically sealed sleeve at least partially enclosing the heating element 106. A hermetic seal 138 also may be provided at the point where power leads 110 enter sleeve 136, in a manner known in the art, in order to allow power leads 110 to operatively connect with heating element 106, while maintaining the overall hermetic seal of sleeve 136. Sleeve 136 may be comprised of a material that is sufficiently flexible and resilient to allow warming pad 100 to be used on an adjustable operating table during surgical procedures involving extreme patient positioning, such as inclined positions, the Trendelenburg position, the reverse Trendelenburg position, and a modified Trendelenburg position. In an embodiment, the sleeve 136 may conduct heat sufficiently well to allow effective warming of a patient during a surgical procedure. In some cases, the sleeve 136 may insulate a patient from heating element 106 sufficiently well to protect a patient from overheating or burns.

Heat Reflecting Layer

With continued reference to FIG. 4, in some examples, a heat reflecting layer 108 may be situated between the heating element 106 and the bottom portion 126. The heat reflecting layer 108 may comprise any heat reflective material known in the art. Exemplary reflective materials can include metal foil materials (e.g., aluminum foil), metalized polyesters (e.g., as used in space blankets and insulated clothing), metalized polyimides, and similar materials. Desirably, the reflecting layer 108 is formed from a material that is sufficiently flexible to allow warming pad 100 to be used on an adjustable operating table during surgical procedures involving extreme patient positioning, such as inclined positions, as discussed hereinabove. Heat reflecting layer 108 may increase the efficiency of warming pad 100 by directing heat from heating element 106 toward a patient disposed on top portion 124, and away from an operating table 102.

Patient Warming System

With reference again to FIG. 1, in some examples, the patient warming device 1 includes the control unit 200, which is removably and operatively connected to warming pad 100 by the leads 212. In some examples, the control unit 200 is configured to adjustably connect to an IV post 204. Alternatively, the control unit 200 can be configured to rest on a table, tray, shelf, or floor depending on the arrangement of the operating room and surgical instruments. The control unit 200 may be configured to allow operating room staff to control power to the heating element 106, and to receive and read temperature data from the temperature sensors 132 situated in an embodiment of warming pad 100. In an embodiment, control unit 200 may include a processor programmed to automatically control the temperature of the heating element 106 based on data returned from temperature sensors 132.

In an embodiment, control unit 200 may serve as a power supply or power regulator for heating element 106. The control unit 200 can receive power from a variety of suitable sources including, for example, AC power from a wall outlet or generator or DC power from a battery. As shown in FIG. 1, a power cord 202 including a plug 224 coupled to an AC adapter is removably connected to the control unit 200. The plug 224 can be plugged into a wall outlet in an operating room. In other examples, a power supply, such as a battery may be used in place of a wall outlet.

Control Unit

Figure 5:
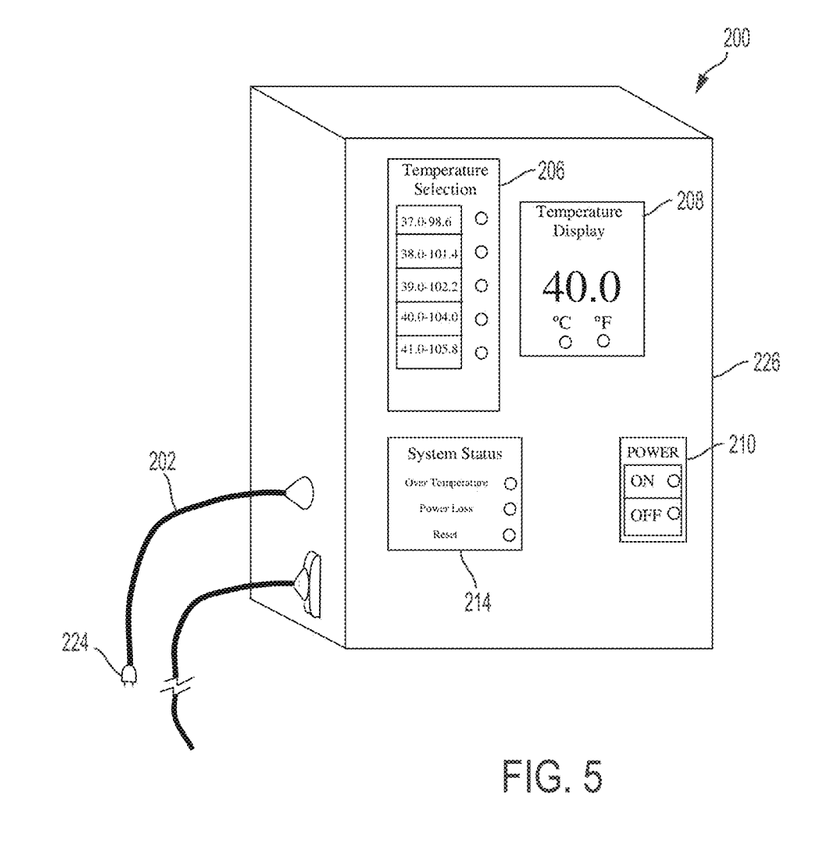
FIG. 5 is an embodiment of a control unit of a patient warming device.

External features of an exemplary control unit 200 for the warming pad are illustrated in greater detail in FIG. 5. Optionally, the control unit 200 includes one or more of a power on/off indicator 210, a temperature indicator display 208, a system status display 214, and a temperature selector 206. The power on/off indicator 210 may be a simple switch including a first portion or button to be pressed to turn the power on and a second portion or button to be pushed to turn the power off. In other examples, the on/off switch can include virtual buttons or soft buttons and/or a touch screen display that can be manipulated by the user to turn the control unit 200 and/or heating element 106 (shown in FIGS. 1-4) on and off. The temperature display indicator 208 can include a display of numeric characters for the measured temperature. The control unit 200 also may include a power control switch, not shown in the figure. The displayed numeric value may be updated at intervals, or in real time, based on temperature data taken by the at least one temperature sensor 132.

In some examples, the temperature selector 206 may include one or more settings allowing a user to choose between one or more ranges of temperature settings. For example, the selector 206 may include a setting for standard body temperature (e.g., 37 C, 98.6° F.), as well as settings for higher temperatures ranging from, for example 38 C (101.4° F.) to 41 C (105.8° F.). The system status display 214 may show at least one status, including an over temperature status, a power loss status, and a reset status. In an embodiment, these displays and selectors may be positioned on a front face 226 of control unit 200, which may provide ease of operation of the patient warming device 1. It should be understood, however, that the configuration of displays and selectors recited herein is not meant to be limiting, and other data or controls known in the art may be included in various embodiments of control unit 200.

As previously described, the control unit 200 may also include a power cord 202 and a plug 224 connected to an AC adapter. The power cord 202 can be configured to draw power from a standard wall outlet. Power cord 202 may include a plug 224, and may connect to control unit 200 via a strain relief 216 known in the art.

As shown in FIG. 5, the power and/or signal leads 212 may operatively connect to control unit 200 by with a connector 218. Power and/or signal leads 212 allow control unit 200 to feed electrical current to warming pad 100, and to receive temperature data from the at least one temperature sensor 132. Power for warming pad 100 and for control unit 200 may be drawn from a wall outlet by means of power cord 202.

Operating Method

In some examples, the processor of the control unit 200 is configured to receive signals representative of a temperature of the warming pad from the temperature sensors 132 (shown in FIG. 3). The processor is configured to process the received signals to obtain a temperature of the warming pad. In some instances, the temperature may be based on information received from a single temperature sensor. In other examples, the processor receives signals from a plurality of temperature sensors on the pad. In that case, the processor may be configured to determine an average temperature value or, in other cases, may record temperature values for different areas of the pad. For example, the processor may record a temperature near the patient's head, a temperature near the patient's torso, and a temperature for portions of the pad which are not in contact with the patient. In some examples, the processor can also receive information from other sensors, monitors, and medical devices at the surgical scene. For example, the processor may receive information about a patient skin or internal body temperature from patient monitoring devices or sensors configured to obtain such information. The processor may also receive physical and demographic information for the patient (e.g., patient height, weight, gender, age, body mass index, body fat percentage, etc.). Patient physical and demographic information can be manually entered by a user of the system or may be automatically downloaded from a database, such as a patient electronic health record database. The processor may use the patient temperature information, patient physical information, and/or patient demographic information to determine whether the warming pad is effectively maintaining the patient's body temperature.

The processor is further configured to compare the determined temperature to one or more threshold values. As discussed above, the threshold value can be a target temperature for the pad manually entered by a user using the control unit 200. In other examples, threshold value(s) may be default values for the control unit 200. For example, the control unit 200 may be set to operate within a range of minimum and maximum safe temperatures, such as a range of between 37° C. and 42° C. In that case, the control unit 200 may be configured to alert a user both when the temperature of the pad 100 has dropped below a safe value (e.g., 37° C.), which may indicate that the pad 100 is not preserving the patients' normal body temperature, and when the temperature is above a threshold value (e.g., 42° C.), which may indicate an unsafe condition. The processor may be further configured to adjust operating parameters for the control unit 200 and/or pad based on results of the comparison between the measured and threshold temperature values. For example, when the comparison indicates that the measured temperature is below a threshold value, the processor may cause the control unit to increase power provided from the control unit to the heating element. Conversely, if the comparison indicates that the measured temperature is above the threshold value, the processor may cause the control unit to decrease power provided by the control unit to the heating element. If the comparison indicates that the measured temperature is within an acceptable range (e.g., within a predetermined percentage of the threshold value), the processor may cause the control unit to continue providing power to the heating element at the same level.

Although patient warming device 1 has been described in detail by illustrative embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

It is to be understood that the invention may assume various alternative variations, except where expressly specified to the contrary. It is also to be understood that the specific devices illustrated in the attached drawings, and described in the specification, are simply exemplary embodiments of the invention. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope thereof. For example, it is to be understood that the present invention contemplates that, to the extent possible, one or more features of any embodiment can be combined with one or more features of any other embodiment. The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

The invention claimed is:

1. A single-use patient positioning and warming pad configured to be placed between a patient and an operating table during a surgical procedure, the pad comprising:
    a viscoelastic foam body comprising a top block formed from a first foam material comprising an open cell foam that absorbs fluid collected on a top surface of the open cell foam, wherein the top surface of the open cell foam is configured to contact the patient, and a bottom block formed from a second foam material, the bottom block comprising a foam bottom surface configured to contact a surface of the operating table during the surgical procedure to maintain positioning of the pad on the table, wherein the first foam material is softer than the second foam material, so that a depression sufficient to maintain positioning of the patient is formed when the patient lays on the pad, and so that the bottom block is sufficiently firm to support the pad and the patient;
    a plurality of temperature sensors positioned within the top block of the foam body;
    a heating element at least partially disposed between the top block and the bottom block of the foam body;
    an electrical connector having a proximal end portion enclosed within the foam body connected to the heating element and a distal end portion extending from the foam body and configured to directly or indirectly connect to a power source and/or control unit for the heating element, wherein the electrical connector comprises a plurality of power leads, each of which is connected to the heating element at a unique connection position on the heating element, and a plurality of sensor leads connected to the plurality of temperature sensors, which are separate from the plurality of power leads within the foam body;
    a protective sleeve enclosing the heating element forming a hermetic seal about portions of the plurality of power leads and hermetically sealing the portions of the plurality of power leads and heating element from the foam body; and
    a synthetic adhesive disposed between an inwardly facing surface of the top block and an inwardly facing surface of the bottom block for mounting the top block to the bottom block thereby enclosing the protective sleeve within the viscoelastic foam body.

2. The pad of claim 1, wherein the viscoelastic foam body has sufficient viscosity and resiliency to maintain positioning of the patient relative to the operating table during surgical procedures in which the operating table is moved to an inclined position.

3. The pad of claim 2, wherein, during the surgical procedure, the operating table is configured to place the patient in one or more of the following positions: a reverse inclined position, a Trendelenburg position, a reverse Trendelenburg position, and a modified Trendelenburg position.

4. The pad of claim 2, wherein an angle of the operating table in the inclined position is between about 30 degrees and 45 degrees.

5. The pad of claim 2, wherein the viscoelastic foam comprises a viscoelastic polyurethane having one or more of:
    a ball rebound of approximately 0.1 percent to approximately 1.9 percent;
    a compression set, for a 25 percent compression, of less than 0.5 percent;
    an air flow of 0.3 to 1.0 cubic foot per minute;
    an indentation force deflection of approximately 10 to approximately 15 pounds;
    a tensile strength of approximately 8 pounds per square inch to approximately 12 pounds per square inch;
    a coefficient of static friction of 0.2 to 1.0; and
    a density of approximately 83 kilograms per cubic meter to approximately 103 kilograms per cubic meter.

6. The pad of claim 1, further comprising a heat reflective layer disposed between the protective sleeve and the bottom block of the viscoelastic foam body.

7. The pad of claim 1, wherein the second foam material of the bottom block portion of the foam body comprises open cell foam.

8. The pad of claim 1, wherein the second foam material of the bottom block of the foam body comprises closed cell foam.

9. A patient warming system comprising:
    a single-use patient positioning and warming pad configured to be placed between a patient and an operating table during a surgical procedure, the pad comprising:
        a viscoelastic foam body comprising a top block formed from a first foam material comprising an open cell foam that absorbs fluid collected on a top surface of the open cell foam, wherein the top surface of the open cell foam is configured to contact the patient, and a bottom block formed from a second foam material, the bottom block comprising a foam bottom surface configured to contact a surface of the operating table during the surgical procedure to maintain positioning of the pad on the table, wherein the first foam material is softer than the second foam material, so that a depression sufficient to maintain positioning of the patient is formed when the patient lays on the pad, and so that the bottom block is sufficiently firm to support the pad and the patient;

a plurality of temperature sensors positioned within the top block of the foam body;

a heating element at least partially disposed between the top block and the bottom block of the foam body;

an electrical connector having a proximal end portion enclosed within the foam body connected to the heating element and a distal end portion extending from the foam body and configured to directly or indirectly connect to a power source, wherein the electrical connector comprises a plurality of power leads, each of which is connected to the heating element at a unique connection position on the heating element, and a plurality of sensor leads connected to the plurality of temperature sensors, which are separate from the plurality of power leads within the foam body;

a protective sleeve enclosing the heating element forming a hermetic seal about portions of the plurality of power leads and hermetically sealing the portions of the plurality of power leads and heating element from the foam body; and a synthetic adhesive disposed between an inwardly facing surface of the top block and an inwardly facing surface of the bottom block for mounting the top block to the bottom block thereby enclosing the protective sleeve within the viscoelastic foam body; and a control unit operatively connected to the power source, the power leads, and the sensor leads, the control unit being configured to control power provided to the heating element from the power source, the control unit comprising:

a cable removably connected to the electrical connector of the heating element for providing power and/or operating instructions to the heating element, and a processor comprising computer-readable memory containing instructions that, when executed by the processor, cause the processor to:

receive and process temperature information from the plurality of temperature sensors;

determine a temperature of the warming and positioning pad based on the received and processed information;

compare the determined temperature to a threshold temperature value; and provide a notification to a user when the determined temperature exceeds the threshold value.

10. The patient warming system of claim 9, wherein the instructions further cause the processor to one of:

increase a power output of the control unit to the heating element when the determined temperature is less than the threshold value; and decrease a power output of the control unit to the heating element when the determined temperature exceeds the threshold value.

11. The patient warming system of claim 9, wherein the viscoelastic foam body has sufficient viscosity and resiliency to maintain positioning of the patient relative to the operating table during surgical procedures in which the operating table is moved to an inclined position.

12. The patient warming system of claim 11, wherein, during the surgical procedure, the operating table is configured to place the patient in one or more of the following positions: a reverse inclined position, a Trendelenburg position, a reverse Trendelenburg position, and a modified Trendelenburg position.

13. The patient warming system of claim 11, wherein an angle of the operating table in the inclined position is between about 30 degrees and 45 degrees.

14. The patient warming system of claim 11, wherein the viscoelastic foam comprises a viscoelastic polyurethane having one or more of:

a ball rebound of approximately 0.1 percent to approximately 1.9 percent;

a compression set, for a 25 percent compression, of less than 0.5 percent;

an air flow of 0.3 to 1.0 cubic foot per minute;

an indentation force deflection of approximately 10 to approximately 15 pounds;

a tensile strength of approximately 8 pounds per square inch to approximately 12 pounds per square inch;

a coefficient of static friction of 0.2 to 1.0; and a density of approximately 83 kilograms per cubic meter to approximately 103 kilograms per cubic meter.

15. The patient warming system of claim 9, wherein the control unit comprises a display, and wherein the instructions cause the processor to cause the display to display a numeric representation of the determined temperature on the display.

16. The patient warming system of claim 15, wherein providing the notification to the user when the determined temperature exceeds the threshold value comprises displaying an over temperature indicator on the display.

* * * * *